(12) United States Patent
Ball

(10) Patent No.: US 11,883,082 B2
(45) Date of Patent: Jan. 30, 2024

(54) METHOD AND APPARATUS FOR IMPROVING BONE SCREW IMPLANTS

(71) Applicant: Bret G. Ball, Lake Oswego, OR (US)

(72) Inventor: Bret G. Ball, Lake Oswego, OR (US)

(*) Notice: Subject to any disclaimer, the term of this patent is extended or adjusted under 35 U.S.C. 154(b) by 442 days.

(21) Appl. No.: 17/064,157

(22) Filed: Oct. 6, 2020

(65) Prior Publication Data

US 2022/0104858 A1  Apr. 7, 2022

(51) Int. Cl.
| | | |
|---|---|---|
| *A61B 17/86* | (2006.01) | |
| *A61F 2/44* | (2006.01) | |
| *A61B 17/56* | (2006.01) | |

(52) U.S. Cl.
CPC .......... *A61B 17/869* (2013.01); *A61B 17/863* (2013.01); *A61B 17/8615* (2013.01); *A61F 2/446* (2013.01); *A61B 2017/564* (2013.01); *A61B 2017/8655* (2013.01)

(58) Field of Classification Search
CPC ... A61B 17/844; A61B 17/846; A61B 17/686; A61B 17/869
See application file for complete search history.

(56) References Cited

U.S. PATENT DOCUMENTS

| | | | |
|---|---|---|---|
| 6,200,345 B1 * | 3/2001 | Morgan | A61C 8/0018 623/10 |
| 8,388,660 B1 | 3/2013 | Abdou | |
| 10,507,041 B2 | 12/2019 | Tsai et al. | |
| 2017/0100177 A1 * | 4/2017 | Kim | A61B 17/864 |

OTHER PUBLICATIONS

Eur Spine J, Evaluation of a transpedicular drill guide for pedicle screw placement in the thoracic spine, May 29, 2003, 11 pages, posted at ncbi.nlm.nih.gov, [online], [site visited Sep. 29, 2020], available from Internet, <URL: https://www.ncbi.nlm.nih.gov/pmc/articles/PMC3468009/>.

Med Sci Monit, Thoracic Pedicle Screw Placement Guide Plate Produced by Three-Dimensional (3-D) Laser Printing, May 19, 2016, 12 pages, posted at ncbi.nlm.nih.gov, [online], [site visited Sep. 29, 2020], available from Internet, <URL: https://www.ncbi.nlm.nih.gov/pmc/articles/PMC4917319/>.

(Continued)

*Primary Examiner* — Olivia C Chang
(74) *Attorney, Agent, or Firm* — Howard Russell

(57) ABSTRACT

Spinal bone anchor attachment device for improving the attachment of a bone screw to skeletal portions of a patient, the device reducing the risk of screw failure, and improving patient outcomes. The device is composed of a biomaterial compatible with bone and provides an enhanced surface area on outer surfaces of the device for engaging the bone, and an enhanced surface area within the device for engaging the bone screw. The device may also have a guiding slanted tip with a bias element for facilitating the placement of the device into bone tissue and rescuing an improper tract. The device may further be used to secure the placement of pedicle screws, and as a component of an intervertebral stabilization system commonly used in spinal fusion surgeries.

13 Claims, 13 Drawing Sheets

(56) References Cited

OTHER PUBLICATIONS

Yu, C., Ou, Y., Xie, C. et al., Pedicle screw placement in spinal neurosurgery using a 3D-printed drill guide template: a systematic review and meta-analysis, Jan. 3, 2020, 31 pages, posted at josr-online.biomedcentral.com, © 2020 BioMed Central Ltd, [online], [site visited Sep. 29, 2020], available from Internet, <URL: https://josr-online.biomedcentral.com/articles/10.1186/s13018-019-1510-5>.

Invibio, Interbody Fusion Devices Made With Peek-Optima™ Polymers, 5 pages, posted at invibio.com, © 2020 Copyright Invibio Ltd., [online], [site visited Sep. 29, 2020], available from Internet, <URL: https://invibio.com/spine/spinal-interbody-fusion>.

J Korean Neurosurg Soc, A Case of Pedicle Screw Loosening Treated by Modified Transpedicular Screw Augmentation with Polymethylmethacrylate, Jan. 31, 2011, 6 pages, posted at ncbi.nlm.nih.gov, [online], [site visited Sep. 29, 2020], available from Internet, <URL: https://www.ncbi.nlm.nih.gov/pmc/articles/PMC3070902/>.

\* cited by examiner

METHOD AND APPARATUS FOR IMPROVING BONE SCREW IMPLANTS

CONTINUITY AND CLAIM OF PRIORITY

This is an original U.S. patent application.

FIELD

The invention relates to an apparatus and methods for improving patient outcomes in the placement of bone screws, and more particularly to an anchor apparatus, and associated methods of use, for facilitating proper placement of, and enhancing stability of spinal and pedicle screws within vertebral columns and other bone structures.

BACKGROUND

Bone screws are used in a variety of surgeries which require implants into the skeletal system of a patient. Bone screws are commonly used to attach implants such as hip replacements, or to attach plates to bone following a traumatic injury. Screw failure resulting from a mispositioned screw can include vascular and neurological deficits (radicular pain, and motor and sensory dysfunction), dural tear, pain, pseudarthrosis, radiculopathy, and pedicle fracture due to instruments loosening bending and pulling out. Additionally, even with a properly positioned bone screw, there is still a risk of screw failure and bone injury due to the screw loosening, screws shifting within the patient, and screws pulling out of the bone (bending). Complications associated with bone screws negatively impact patient outcomes and generally require additional surgeries to repair.

Pedicles are short projections of bone that come directly off the back of vertebral bodies. Each pedicle lies between the back of each vertebral body and what is known as a transverse process. There are two pedicles per vertebra, one on each side of the spinal cord. Outer cortical, or compact, bone material of each pedicle defines a channel of softer cancellous bone through which a spinal stabilization screw may advantageously pass through and into a cortical and cancellous bone portions of the vertebral body. Since each pedicle is essentially elliptical in cross-section shape, wherein the cortical bone forming a circumference of the ellipse encloses softer cancellous bone of the pedicle, it will be appreciated that there are upper and lower larger area portions of the channel of the pedicle comprising cancellous bone material which does not provide a sufficiently rigid upper and lower structure for strong engagement of a pedicle screw. Therefore, it is common for pedicle screw placements to be come loose over time as forces associated with bending, twisting, and stretching movement of a person having received a spinal stabilization surgery. Accordingly, means for improving the engagement of a pedicle screw with the cortical bone sides of the channel of the pedicle, which sides are closer to the screw than upper or lower portions of cortical bone of the pedicle, would be advantageous.

Bone screws, and in particular vertebral pedicle screws, are also commonly used in vertebral fusion surgeries to treat back pain. Back pain is among the most common medical problems experienced by individuals as they age and has a variety of different causes including degenerative disc disease, trauma, ruptured or bulging discs, arthritis, and sciatica, among other causes. In many cases, including in cases of degenerative disc disease, one of the most common causes of back pain, spinal fusion surgery is used to alter the distribution of weight along the spine, as to relieve pressure in discs and reduce a patient's back pain. Such surgeries generally require the use of bone screws in order to facilitate the alteration of the bone structure as required for a positive patient outcome. In the United States alone it is estimated that surgeons perform over 1.62 million instrumented spinal fusions surgeries per year, with compilations reportedly resulting from pedicle screws occurring in approximately 2.5% of cases. Further, it is estimated that there may up to a 24% error in placement of pedicle screws, which often results in multiple receiving channels having to be created, as with a piercing tool, into a patient's spine, or improperly placed screws having to be removed and replaced in the proper location. Accordingly, pedicle screw complications impact thousands of patients each year.

Bone screws used in spinal surgery are referred to as vertebral pedicle screws, and they have been used in spinal surgeries for decades. Vertebral pedicle screws are implanted into the vertebral pedicle, a dense stem-like structure which projects adjacent the posterior of the spine. Vertebral pedicle screws are often used in spinal surgery to correct deformity, treat trauma, to affix rods or plates to the spine, and to assist in holding bony structures together in spinal fusion surgeries. Vertebral pedicle screws are most often used in the lumbosacral spine, but can also be implanted into the thoracic, sacral, and cervical vertebrae where necessary. Vertebral pedicle screws serve to anchor bone tissue together by engaging the hard-cortical bone surface along the pedicle and in the vertebral body to the surface of the screw, primarily along the threads which engage the bone surface.

Vertebral pedicle screws are usually implanted in the spine of a patient with use of imaging techniques such as x-ray or fluoroscopy to determine the proper depth and angle for screw placement. Once the proper screw placement has been ascertained, a receiving channel has been created, as with a piercing tool, from the surface of the skin and into the vertebral pedicle, whereupon the screw has been inserted. However, even with the use of proper imaging techniques, improper forming of the receiving channel and screw mispositioning have remained significant risks of spinal surgery, and they have often resulted in serious complications to the patient. Not only have complications resulted from a mispositioned screw, again having included vascular and neurological deficits (radicular pain, motor and sensory dysfunction), dural tear, pain, pseudarthrosis, radiculopathy, and pedicle fracture, and screw bending due to instruments loosening and pulling out, but even properly positioned pedicle screws have failed over time. Such risk of failure of properly positioned screws have included the possibility of screw failure and pedicle injury due to screws having loosened, screws having shifted within the patient, screws having pulled out of the pedicle (bending), which have occurred with the passage of time due to inadequate bone to screw interface, and these conditions have resulted in similar complications and poor patient outcomes.

Current bone screws presently used to affix bone implants, including pedicle screws used in spinal fusion surgeries, generally have not provided an adequate surface area interaction between the cortical bone surface of the bone and the screw, which is why screw failure has occurred, and such has been increasingly likely to occur the longer a pedicle screw has remained in place. Complications associated with pedicle screws have been especially noteworthy in patients that have required long vertebral fusions (e.g. 6-7 vertebral fusions). In such cases, the pedicle screws at the top of the vertebral fusion case have been placed under abnormally high stress and have been highly prone to screw failure, wherein prior art pedicle screws have failed to provide a permanent solution for patients experiencing back pain who have required long vertebral fusions.

Further, current pedicle screws used in spinal fusion surgeries generally have not provided for a reliable method of insertion into a receiving channel where an improper receiving channel has occurred. In such cases, it has been difficult to align the pedicle screw into a properly formed receiving channel (after an improperly created receiving channel has occurred), and the pedicle screw has therefore lacked support along a correctly-formed surface of the correctly-formed channel closely adjacent the improperly positioned channel. This has increased the risk of screw insert failure due to reduction of cortical bone surface area, and it has also raised the risk of complications with the surgery because it has been difficult to place a screw in the proper channel when an improper channel has been formed, as with a piercing tool.

As such, there remains a need in the art for an attachment device which will promote the attachment of bone screws, and especially vertebral pedicle screws, to the cortical surface of the bone in order to reduce the risk of complications, and to improve both short-term and long-term patient outcomes, preferably without requiring removal of the bone screw. Additionally, attachment devices that help to facilitate the accurate placement of pedicle screws will also reduce the difficulty of spinal fusion surgeries and improve patient outcomes.

SUMMARY

In accordance with an aspect and an embodiment of the present disclosure, there is provided a spinal bone anchor attachment device (hereafter also referred to as the "device", the "anchor device", or the "anchor attachment device") adapted for use multilaterally with and engaging of a pedicle screw, adapted to increase the surface area interaction between the pedicle screw and the cortical bone in order to provide a permanent attachment of the screw to the bone, to thereby enhance engagement of the screw and device with spinal bone, and thereby enhance sturdiness of a vertebral stabilization procedure. These features and benefits of the device all serve to improve patient outcomes by preventing the breaking out of the screw in the spinal bone during installation and thereafter during later use.

The device in accordance with an aspect of the disclosure and an embodiment comprises an elongated multi-laterally split partial base portion that is split along, and adapted for insertion of the pedicle screw along, a central longitudinal axis of the partial base portion, and an elongated multi-laterally split partial shaft portion preferably split along, and preferably sharing the same split as the base portion, adapted for insertion of the pedicle screw along a central longitudinal axis of the partial shaft portion. The partial shaft portion is split into at least a first side and a second side, and it preferably has an elongated concave inner surface within the partial shaft portion being adapted for engaging the pedicle screw. Further, the device comprises: a tip connecting the lateral sides, e.g., the first side and the second side, of the split partial shaft portion, the tip being positioned opposite the partial base portion, and a plurality of bone engaging ridges, as in preferably a plurality of courses of bone engaging ridges, extending outwardly from and along at least a portion of the length of the partial shaft portion. The partial base portion, the partial shaft portion, and the tip, are adapted to cause the anchor attachment device to expand apart upon subsequent installation of a pedicle screw to better engage an inner cortical bone portion of the pedicle, and thereby enhance sturdiness of the vertebral stabilization procedure.

The device is preferably composed of a compatible biomaterial, including a polymer such as Polyether-ether-ketone (PEEK). The partial shaft portion may be generally octagonal, cylindrical, or ovoid in cross-section shape, or may be in the cross-section shape of another polygonal prism, though comprising a split within the sides of the device, and these such optional cross-section shapes may also be inclusive of the bone engaging ridges.

At least one of the plurality of bone engaging ridges, or preferably plurality of bone engaging ridges, of the device may be comprised of a first edge, or surface, extending outwardly, at least one such first edge, or surface, from each the first side and the second side of the partial shaft portion, and at least a second edge, or surface, such a second edge, or surface, connected to a corresponding at least one first edge, the second edge interconnecting the at least one first edge to a corresponding one of the first side and the second side of the partial shaft portion. Optionally, the first edge may extend perpendicularly from the first and second sides of the partial shaft portion. Further, optionally, there may be provided additional edges, or surfaces, such as a third edge and a fourth edge, each tending toward interconnecting the second edge to each the first side and the second side of the partial shaft portion. Thus, optionally, the first edge comprises a flat bottom edge, the second edge comprises a flat edge that intersects the first edge at approximately a 90-degree angle (substantially parallel to the partial shaft portion), and the third edge then either interconnects the second edge at approximately a 45-degree angle between the second edge and the partial shaft portion, or further, optionally, a fourth edge, or surface, may interconnect the third edge (e.g., the approximately 45-degree-angle edge) with the partial shaft, with the fourth edge being normal to and interconnecting perpendicularly with the partial shaft. Thus, the configuration of the bone engaging ridges may vary without departing form the scope and spirit of the invention as claimed, the primary criteria being that the bone engaging ridges serve to "bite" into cortical bone of a pedicle as a screw is inserted.

Further, in accordance with an aspect and an embodiment of the disclosure, at least one of the plurality of bone engaging ridges may preferably extend with an interior flat surface portion laterally across the concave surface of the partial shaft portion. Each of the plurality of bone engaging ridges may be equidistant from another of the plurality of bone engaging ridges. The plurality of bone engaging ridges may comprise between 12 and 18 bone engaging ridges. In a particular embodiment, a spinal bone anchor attachment device may comprise 15 bone engaging ridges. The number of bone engaging ridges in a particular embodiment, however, will depend on the size of the ridges and the length of the device, and may vary.

In accordance with an aspect and embodiment of the disclosure, alternatively, each of the plurality of bone engaging ridges may extend with an interior flat surface portion, or portions in an alternative embodiment, laterally across the concave surface of each the first side and the second side of the partial shaft portion to form a plurality of cavities, one cavity in between each flat surface portion of each of the ridges on each the first side and the second side of the partial shaft. In an alternative embodiment, each of the plurality of bone engaging ridges may extend along only each the first side and the second side of the partial shaft portion.

In accordance with an aspect and embodiment of the disclosure, the tip may further comprise a bias element adapted for guiding proper placement of the anchor attachment device and the screw into the spinal bone (vertebral body, cortical surface, pedicle, etc.). The bias element may comprise an enhanced angled outer or exterior surface (exterior in the sense that it is adapted to face away from the spinal cord during installation) of the tip relative to the partial shaft portion and adapted for enhanced guiding of the spinal bone anchor attachment device and the screw to proper placement during installation into the pedicle.

In accordance with an aspect and embodiment of the disclosure, the tip may further comprise a point at a leading end of the tip, a first plurality of slanted, or faceted, interior surfaces (interior in the sense that the surfaces are on a side of the tip adapted to be facing inwardly toward the spinal cord upon installation), each of the first plurality of faceted surfaces extending partially from corresponding ones of each the at least first side and the second side of the partial shaft towards the point, and a second plurality of differently slanted, or faceted, interior surfaces (also interior in the sense that the surfaces are on a side of the tip adapted to be facing inwardly toward the spinal cord upon installation) which are non-coplanar with the first plurality of faceted surfaces, each of the second plurality of faceted surfaces of the tip extending further from corresponding ones of the first plurality of faceted surfaces to the point. The first plurality of faceted surfaces may be symmetrical relative to the point and the first side and the second side of the partial shaft portion, and the second plurality of faceted surfaces may also be symmetrical relative to the point and the first side and the second side of the partial shaft portion.

In accordance with an aspect and embodiment of the disclosure, the tip of the device may further comprise a third plurality of laterally exterior faceted surfaces extending from one of each the first side and the second side of the partial shaft towards the point. Still further, the tip of the device may further comprise a fourth plurality of exterior faceted surfaces differently slanted than (i.e., they are non-coplanar relative to) the third plurality of exterior faceted surfaces and extending from corresponding ones of each of the third plurality of exterior faceted surfaces to the point. Preferably more exterior portions of the first and second pluralities of interior faceted surfaces form medial edges with more interior portions of the third and fourth plurality of exterior faceted surfaces—thus defining upper and lower cutting edges of the tip—and wherein preferably the plurality of bone engaging ridges extend outwardly from and along the entire length of the partial shaft portion but do not extend outwardly along any tip portion.

Thus, the device may be partially defined by exterior portions of the first and second pluralities of interior surfaces and interior portions of the third and fourth pluralities of exterior surfaces to form medial cutting edges of the tip extending from the point.

In accordance with an aspect of the disclosure, one or more of the embodiments of the spinal bone anchor attachment device hereof are adapted for use multilaterally with and engaging of a pedicle screw as part of an intervertebral stabilization system comprising a plurality of pedicle screws, an intervertebral stabilization element coupling at least two adjacent pedicle screws anchored to adjacent vertebra, a plurality of spinal bone anchor attachment devices, each device adapted for engaging with a pedicle screw, where each of the plurality of pedicle screws is inserted into a corresponding one of the plurality of anchor attachment devices, and wherein each of the plurality of anchor attachment devices is inserted through a pedicle into a vertebral body. In such a system, each device comprises a multi-laterally split partial base portion split along, and adapted for insertion of one of the plurality of pedicle screws along, a central longitudinal axis of the partial base portion, an elongated multi-laterally split partial shaft portion split along, and adapted for insertion of one of said plurality of pedicle screws along, a central longitudinal axis of said partial shaft portion, said partial shaft portion being split into at least a first side and a second side, an elongated concave inner concave surface within said partial shaft portion adapted for engaging a pedicle screw, an edged tip interconnecting the first side and the second side, opposite said partial base portion, and a plurality of bone engaging ridges extending outwardly from and along the longitudinally extending length of said at least a first side and a second side of said partial shaft portion.

The present invention addresses various problems of prior pedicle screw and spinal fixation systems sometimes failing to permanently attach to the vertebral body without loosening, pulling out, or causing vertebral fracture. In accordance with one or more aspects of the present disclosure, a spinal bone anchor attachment device is provided which is adapted for use multilaterally with and engaging of a pedicle screw. Thus, the device is adapted to increase the surface area interaction between the pedicle screw and the cortical bone, to thereby help enhance engagement of the screw and device with the spinal bone, to avoid breaking out of the screw in the spinal bone during installation and thereafter while in use by the recipient of the procedure. Thus, the benefits of the device of the present disclosure serves to improve both short-term and long-term patient outcomes. In addition, embodiments of the present disclosure also provide such a device which assists a surgeon in the placement of a bone screw, including in cases where there has been an improper receiving channel formed which presents a high risk of complications to the patient.

In accordance with another aspect of the disclosure, there is provided a method for improving patient outcomes in spinal fusion surgery using the spinal bone anchor attachment device of present embodiments. The method may comprise: providing a pedicle screw, providing a spinal bone anchor attachment device for coupling to a pedicle screw, making an incision with a piercing member creating a pilot tract extending from the skin surface of a patient through a pedicle and into an associated vertebral body, inserting the anchor attachment device into the incision with the split along the central longitudinal axis of the partial shaft oriented with one longitudinal portion, or side, of the partial shaft adapted to be deflected upwardly toward the patient's head, with another longitudinal portion, or side, of the partial shaft adapted to be deflected downwardly toward the patient's feet, with a central longitudinal axis of the anchor attachment device positioned laterally relative to the spine, and inserting the pedicle screw into the anchor to deflect the first side and the second side of the partial shaft portion to engage with inner cortical bone portions of the pedicle.

The foregoing method aspect of the disclosure addresses various problems of prior pedicle screw and spinal fixation system methods which have sometimes failed to effectively stay firmly attached to the vertebral body without loosening, pulling out, or causing vertebral fracture. Thus, this method is adapted to increase the surface area interaction between the pedicle screw and the cortical bone, to thereby help enhance engagement of the screw and device with the spinal bone, to avoid breaking out of the screw in the spinal bone during installation and thereafter while in use by the recipient of the procedure. Thus, the benefits of the device and method of the present disclosure serve to improve both short-term and long-term patient outcomes. In addition, this method may also assist a surgeon in the placement of a bone screw, including in cases where there has been an improper receiving channel formed which presents a high risk of complications to the patient. This is in part because the threads of the screw may find more traction in an inner portion of the anchor attachment device than they would going through cancellous bone material, especially where the biased tip of the anchor attachment device would help to guide the device and the screw into a correctly formed tract.

The subject matter of the present invention is particularly pointed out and distinctly claimed in the concluding portion of this specification. However, both the organization and method of operation, together with further advantages and objects thereof, may best be understood by reference to the following descriptions taken in connection with accompanying drawings. For sake of consistency and ease of interpretation, the drawing views below are referenced to human anatomy in all cases, both where human anatomy is depicted and in reference to the preferred placement of a spinal bone anchor attachment device within human anatomy (whether human anatomy is otherwise depicted or not). Thus, in those cases where human spine or back portions are depicted, reference to top, bottom, front, back, and side, each refer to such positions as one would normally consider referencing the human body (e.g., with the stomach side being the front (anterior), and the back side being the back (posterior)). And in those cases where a spinal bone anchor attachment device is depicted itself, alone, without any part of the human body being referenced, a similar reference is used according to how the device would be placed in a human body generally speaking. Thus, views of an elongated longitude of the device will be considered side views generally, as the device would be viewed as generally elongated as viewed from a human being's side. Thus, it will be appreciated that a back view of the spinal bone shim attachment device are considered from the perspective of a human back (referencing normal placement of the device in a human spine), whereas side and top views of the device are considered relative to the most likely placement of the device in a human body as well, from the side (side view) and head (top view), respectively.

BRIEF DESCRIPTIONS OF DRAWINGS

Figure 9A:
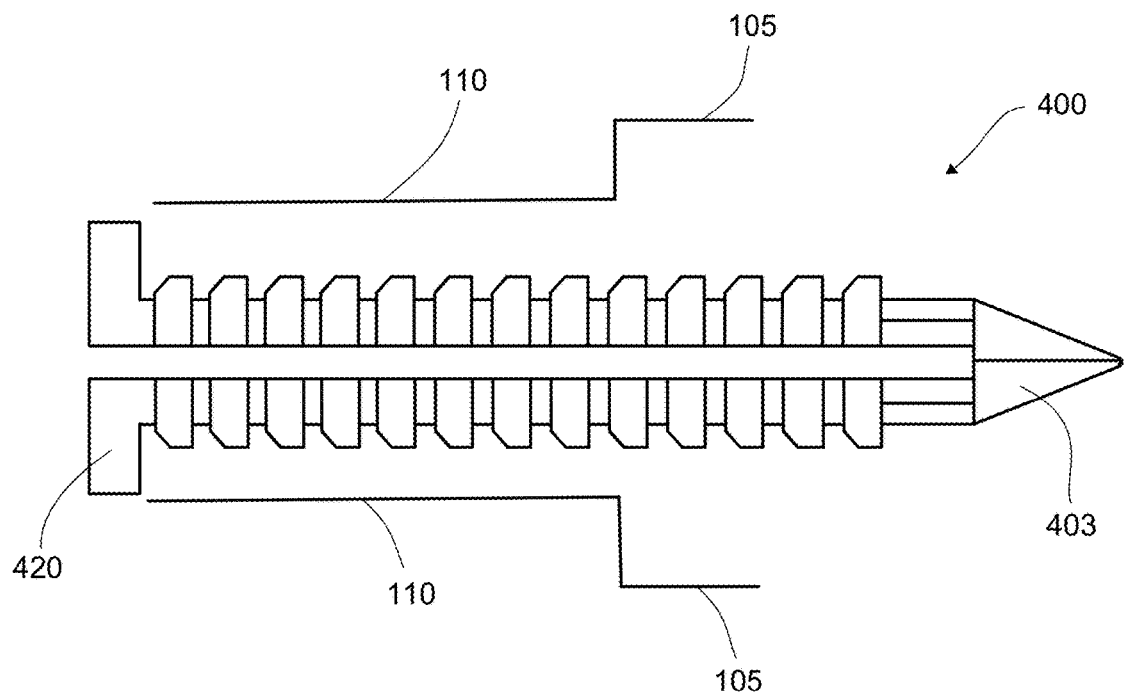

FIG. 9A shows a right-side view (though the left-side view would look the same) of the spinal bone anchor attachment device in accordance with one or more aspects and embodiments of the disclosure, showing how it would be inserted into a representative pedicle and vertebral body, and without a pedicle screw inserted. As viewed in FIG. 3A, it will be appreciated that this and other views have been normalized somewhat to give true side and other views of the device, since from the side of a patient, a longitudinal axis of a pedicle would actually extend upwardly, from along the back of the patient to their front, and inwardly toward the spinal cord, from along a more outward location of the patient to a more inward location of the patient.

Figure 9B:
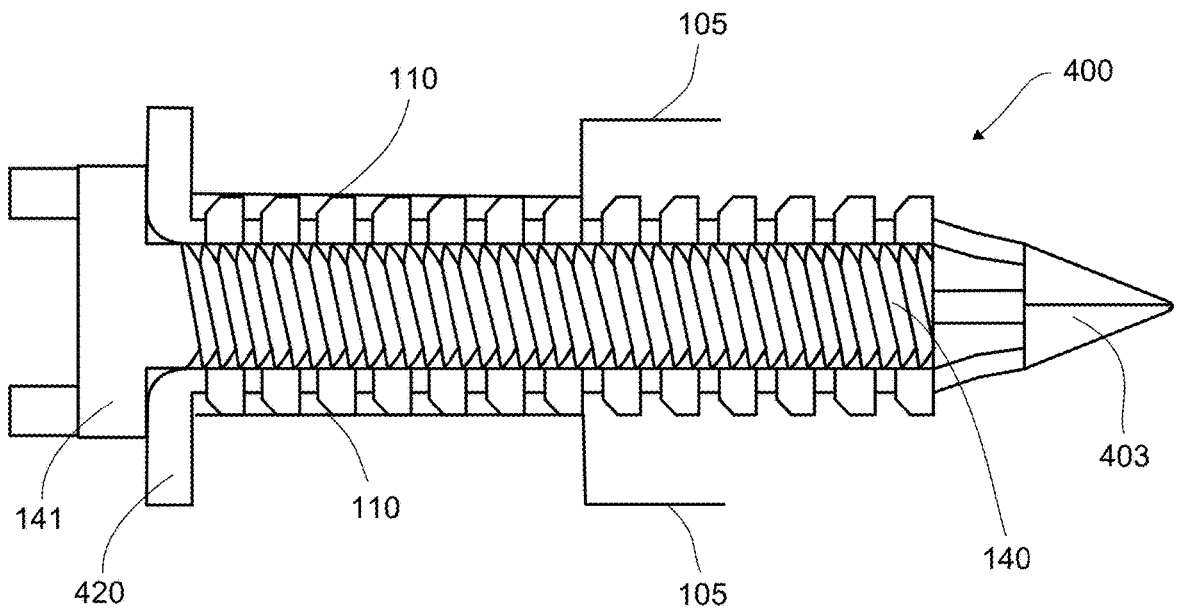

FIG. 9B shows a longitudinal cross-sectional view of a spinal bone anchor attachment device in accordance with one or more aspects and embodiments of the disclosure, showing how it would be inserted into a representative pedicle and vertebral body, and with associated displacement of the device as a result of an inserted pedicle screw.

DETAILED DESCRIPTION

Figure 1:
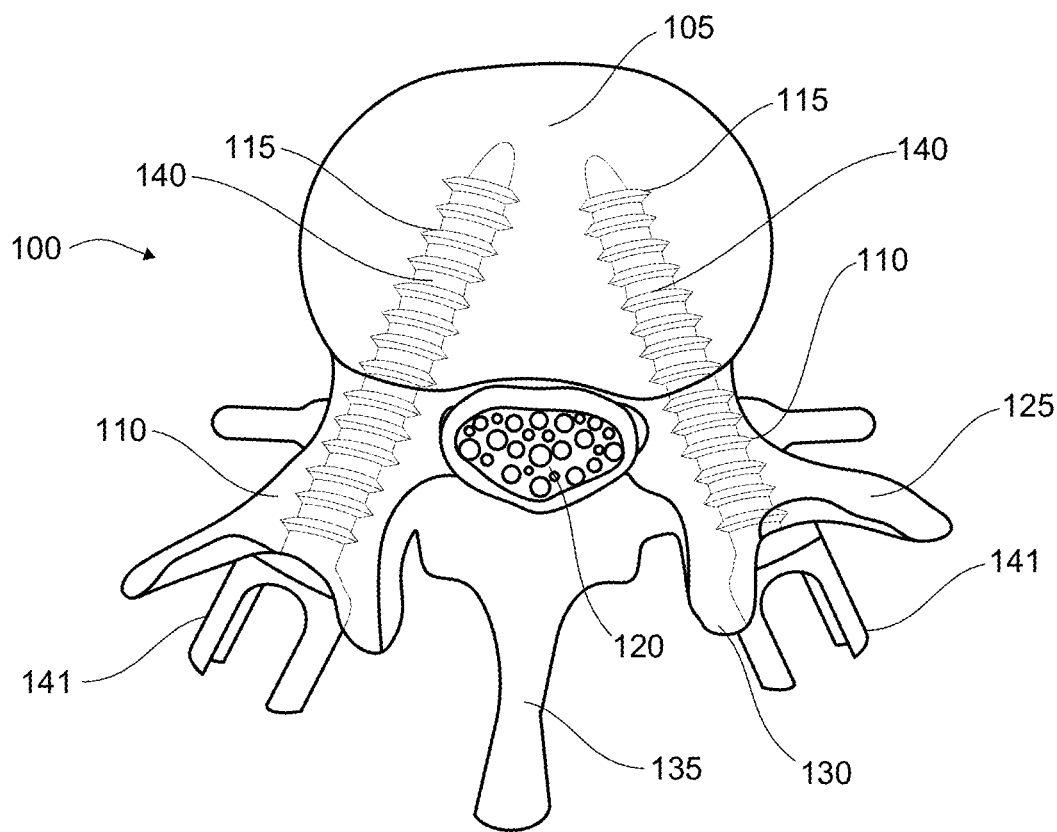
FIG. 1 shows a lateral cross-section top view of a thoracic vertebra and how two pedicle screws would be properly inserted into the vertebra, as set forth within the prior art.

Referring to the Figures, FIG. 1 shows a cross sectional view of prior art pedicle screws 140 inserted into a region of the thoracic spine portion 100. The pedicle screws are inserted through the vertebral pedicle 110 and into the vertebral body 105, with the threads 115 of the screws engaging the hard-cortical bone along pedicles, and cortical rim surrounding the vertebral body 105. While the pedicle screws will also engage the cancellous bone within the pedicle 110 and vertebral body 105, it is the narrowed cortical bone portion of the pedicle which bears most of the load applied to the spine, and which will bear most of the load applied by the pedicle screws. Depending on the location of the spine in which the screw is inserted, there may be a transverse process 125, an articular process 130, and a spinus process 135 near the base of the screw.

When placing the pedicle screws 140, it is critically important to create a receiving channel, as with a piercing tool, that goes through the center of the pedicle bone Ho and into the center mass of the vertebral body 105, and which does not pass through the spinal cord 120. Damage to the spinal cord 120 results from screw placement angled too close to the center of the spine, and this may lead to nerve injury resulting in paralysis of the patient. Improper screw placement can also result from a receiving channel which is formed at an angle which places the screw too far to the edge of the pedicle and places the screw at a location away from the center mass of the vertebral body (e.g., as shown by receiving channel 703 shown in FIG. 7). Such improper placement of the screw 140 at too wide an angle not passing through the center of the pedicle 110 and into the center mass of the vertebral body 105 must be re-created and the screw re-placed in order to ensure a positive patient outcome.

Figure 2:
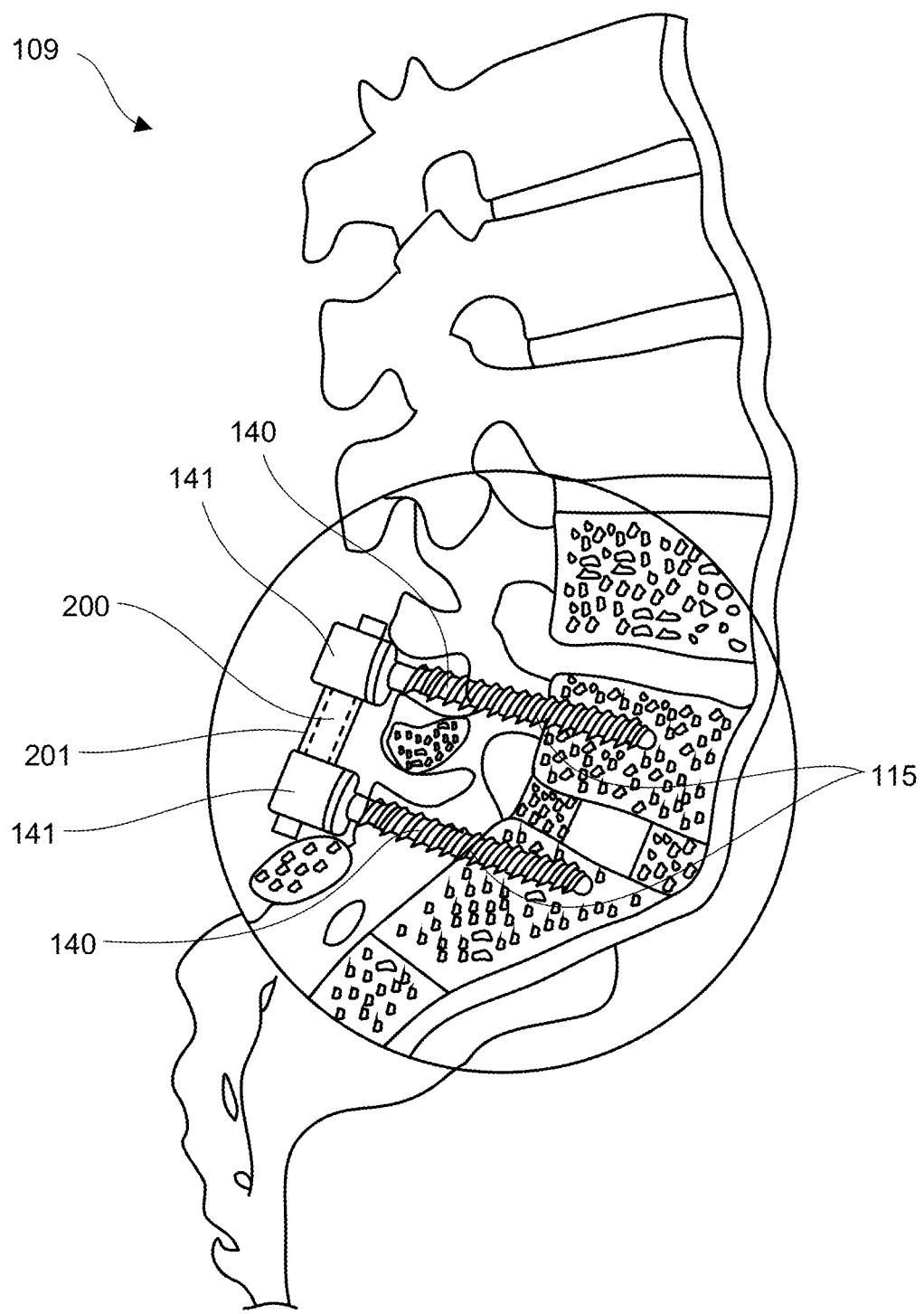
FIG. 2 shows a longitudinal partial cross-section side view of the lumbar spine and how two pedicle screws would be properly inserted into the vertebrae and bound together as a part of an intervertebral stabilization system, as set forth within the prior art.

FIG. 2 shows a longitudinal cross-section side view of the lumbar spine 109 with two prior art pedicel screws 140 properly inserted and bound together as a part of an intervertebral stabilization system. The pedicle screws 140 are inserted through the pedicle 110 and into the vertebral body 105, with the threads 115 primarily engaging an inner cortical surface of the pedicle bone. Following proper insertion of a pedicle screw as part of an intervertebral stabilization system, cross members 200 (i.e., known as cords, and with spacers 201 between heads 141 of the pedicle screws 140) connecting the various pedicle screw heads 141 to immobilize the vertebrae and allow for a successful vertebral fusion at the location of the intervertebral stabilization system.

Figure 3A:
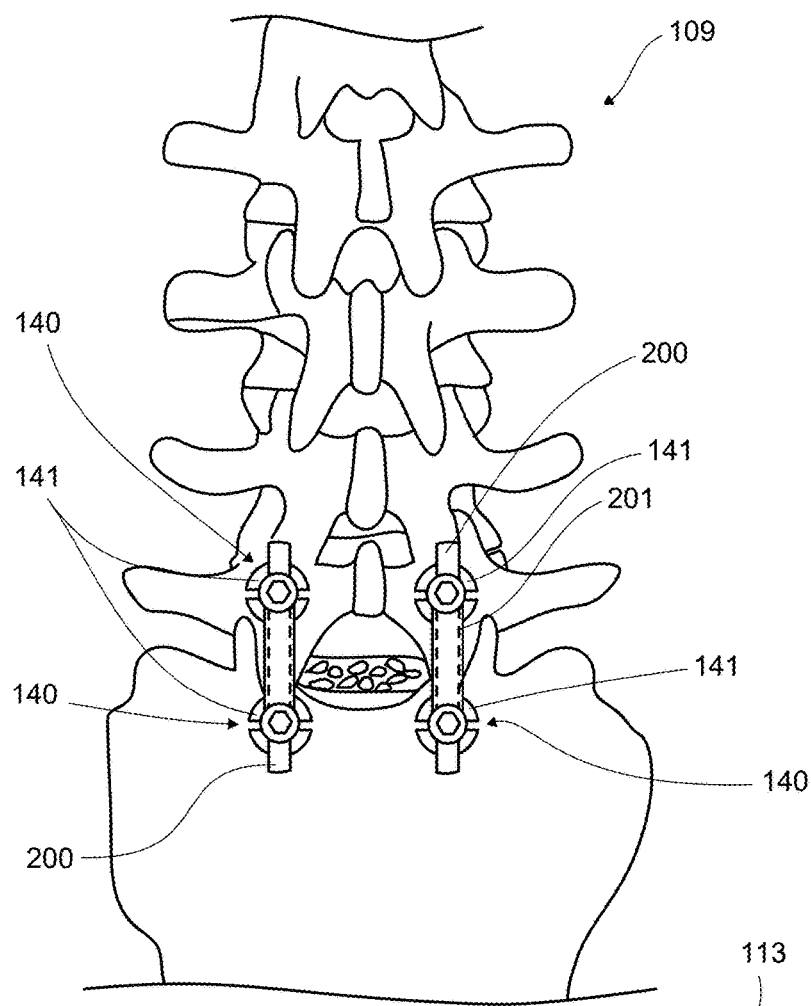
FIG. 3A shows a back longitudinal view of a lumbar spine and how four pedicle screws would be inserted into the vertebrae and bound to each other on the right and left side of the spine as a part of an intervertebral stabilization system, as set forth within the prior art.
Figure 3B:
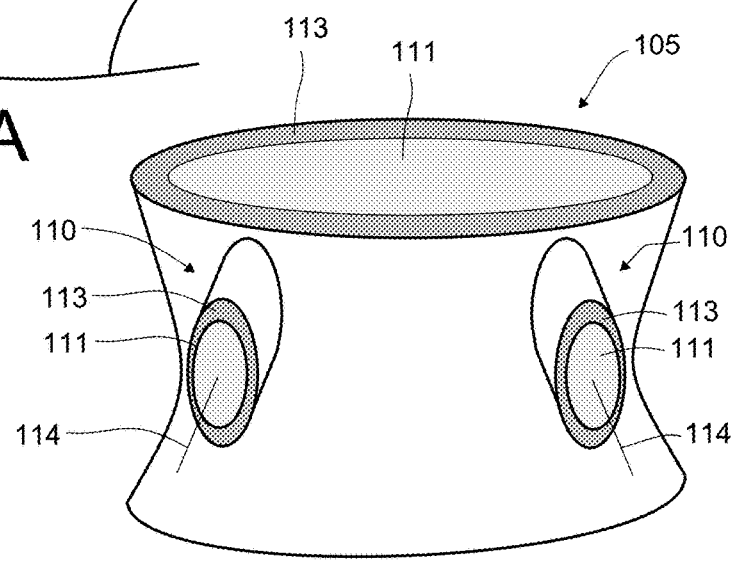
FIG. 3B shows a representative diagram of a mostly posterior, or back view, of a lumbar thoracic vertebra further indicating an oblong oval cross-section shape and axis of pedicles through which pedicle screws pass during a vertebral stabilization process.

FIG. 3A shows a back-facing view of the lumber spine 109 with four prior art pedicle screws 140 inserted and bound to each other with cross members 200 and spacers 201 on the right and left side of the spine as a part of an intervertebral stabilization system. The pedicle screws 140 are inserted through the pedicle 110 and into the vertebral body 105 (see FIGS. 1 and 2 for further reference), with the threads 115 (FIGS. 1 and 2) engaging the inner cortical surface of the pedicle bone. FIG. 3B shows a representative diagram of a mostly posterior, or back view, of a lumbar thoracic vertebral body 105, further indicating a typical oblong oval cross-section shape and pedicle longitudinal axis 114 of the pedicles 110 and inner cancellous (softer) bone 111 through which pedicle screws pass during a vertebral stabilization process, whereas cortical (harder) bone 113 of the pedicle and vertebral body are also indicated. Because of this structure of pedicles 110, prior art vertebral stabilization pedicle screws have not always had sufficient engagement to cortical bone 113, and therefore some have loosened over time. This has been because with the oblong oval cross-section shape has a diameter that is longer in a Y-axis direction as viewed from a patient's back than its X-axis diameter, has made it so that a bulk of the stress on the pedicle screws 140 has had to be supported by softer cancellous bone 111 along that Y-axis, whereas with prior art systems the engagement of the screw threads 115 on the lateral (in an X-axis direction) has sometimes not been sufficient to withstand the stresses of repeated bending, sitting, standing, twisting, etc., of the patient over time.

Figure 4A:
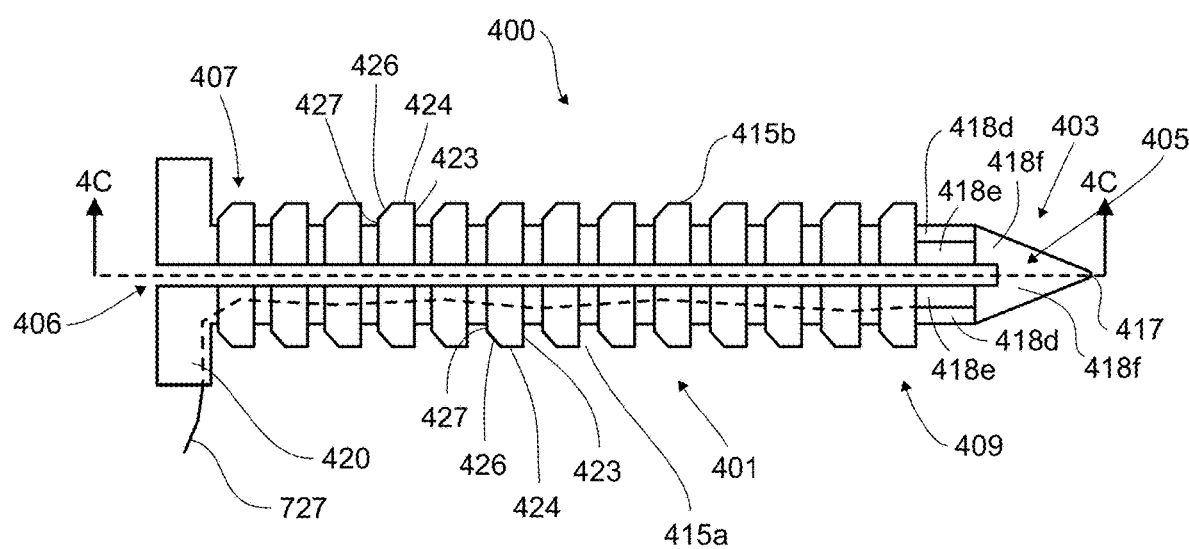
FIG. 4A shows a right side view (considering placement of the device on the right side of a person's spine as viewed from their back) of the spinal bone anchor attachment device in accordance with one or more aspects and an embodiment of the disclosure and showing that the device has a multi-laterally split partial shaft.
Figure 4B:
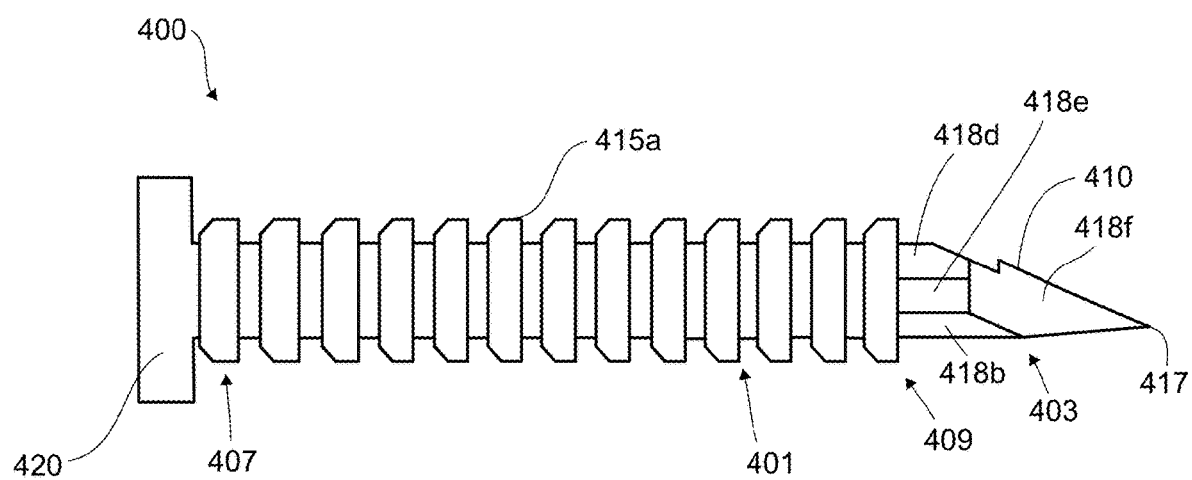
FIG. 4B shows a bottom view (considering placement of the device on the right side of a person's spine as viewed from their back) of the spinal bone anchor attachment device of FIG. 4A in accordance with one or more aspects and an embodiment of the disclosure.
Figure 4C:
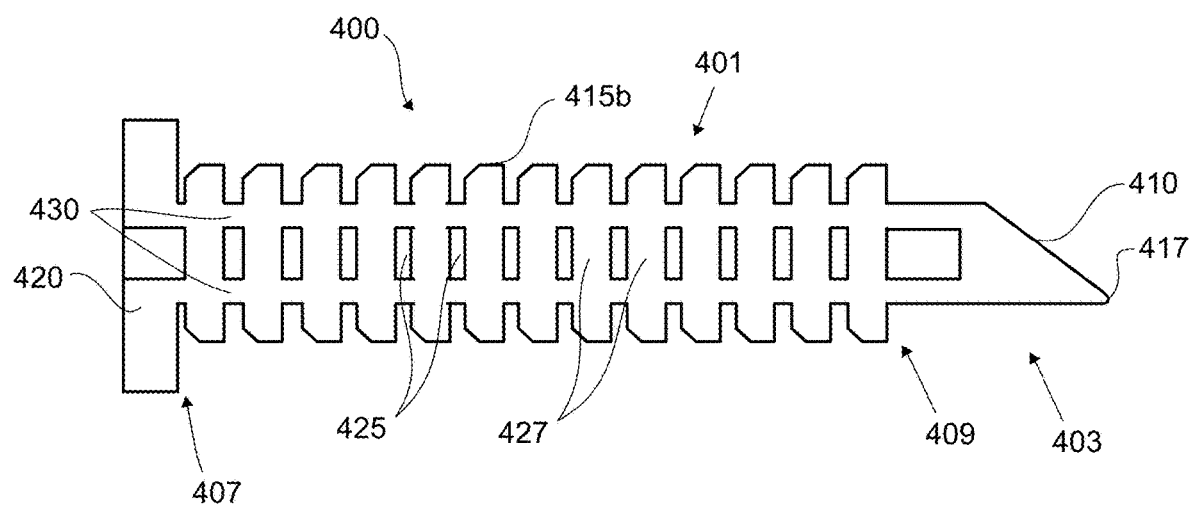
FIG. 4C shows a bottom section view (considering placement of the device on the right side of a person's spine as viewed from their back) of the spinal bone anchor attachment device and looking along section line 4C-4C of FIG. 4A.

Referring to FIGS. 4A-4C there is shown a preferred embodiment of a spinal bone anchor attachment device 400 in accordance with one or more aspects of the disclosure. The device 400 comprises split generally semicircular (in cross section) base 420, split at 406, and a split shaft 401 also preferably split at 406 for most of the length of the shaft down the longitudinal center of the device. The split shaft 401 has two ends, a first end 407 adjacent where the base 420 is attached, and a second end 409 opposite the first end. There is provided a tip 403 attached adjacent the second end 409 of the split shaft 401, such that the split 406 ends just before, or at, the tip. In this way the base 420 and the split shaft 401 are capable of being split apart at 406, or deflected outwardly, upon the insertion of a bone screw 140.

The split shaft 401 of the device 400 preferably comprises a lower portion 411 and an upper portion 413. Preferably along the lower portion 411 of the split shaft 401, there are a plurality of courses of bone engaging ridges 415a, each bone engaging ridge extending around the generally circular (or octagonal, polygonal, etc.) outer periphery of the lower portion 411 of the split shaft 401 such that each course 415a extends outwardly generally perpendicularly to the longitudinal axis of the partial split shaft 401. The plurality of courses of bone engaging ridges 415a also preferably run (each course perpendicularly to the longitudinal axis of the split shaft 401 as described above), each course evenly spaced from one another and repetitively spaced along the entire length of the lower portion 411 of the split shaft 401. These courses of bone engaging ridges 415a may also be referred to as knurling 415a, Preferably each course of the plurality of bone engaging ridges 415a comprises a generally semi-circular (or octagonal or other rectangular or polygonal shape as viewed in cross section) contiguous ridge extending from the split 406 at one lateral edge of the lower portion 411 of the partial shaft 401 adjacent the split 406, with each bone engaging ridge 415a extending therefrom around the lower portion circumference of the split shaft 401 to an opposing another lateral edge of the lower portion adjacent the split 406.

Further, preferably along the upper portion 413 of the split shaft 401, there are another plurality of courses of bone engaging ridges 415b, each bone engaging ridge extending around the generally circular (or octagonal, polygonal, etc., when viewed in cross section) outer periphery of the upper portion 413 of the split shaft 401 such that each course 415b extends outwardly generally perpendicularly to a longitudinal axis of the partial split shaft 401. The plurality of courses of bone engaging ridges 415b also preferably run (each course perpendicularly to the longitudinal axis of the split shaft 401), each course evenly spaced from one another and repetitively spaced along the entire length of the upper portion 413 of the split shaft 401. These courses of bone engaging ridges 415b may also be referred to as knurling 415b.

Preferably each course of bone engaging ridges 415b comprises a generally semi-circular (or octagonal or other rectangular or polygonal shape when viewed in cross section) contiguous ridge extending from the split 406 at one lateral edge of the upper portion 413 of the partial shaft 401 adjacent the split, with each bone engaging ridge 415b extending therefrom around the upper portion circumference of the split shaft 401 to an opposing another lateral edge of the upper portion adjacent the split 406. The split shaft 401 may be split into more than two sides which run most of the length of the device 400 and the split shaft may come in a variety of sizes to accommodate placement of bone screws 140 in a variety of locations (e.g. in any location where bone screws coming loose may be a problem) and in patients of various size with differing anatomy and bone structure. A non-exhaustive range of possible dimensions for the device 400 and the shaft 401 may include the range of 3.5 mm×20 mm to 9.5 mm×60 mm. The general cross-section shape of the split shaft 401 and split base 420 may be ovoid in shape, or may be in the shape of a polygonal prism, such as an octagonal prism with a gap or void area between the portions of the split base and split shaft.

Figure 4D:
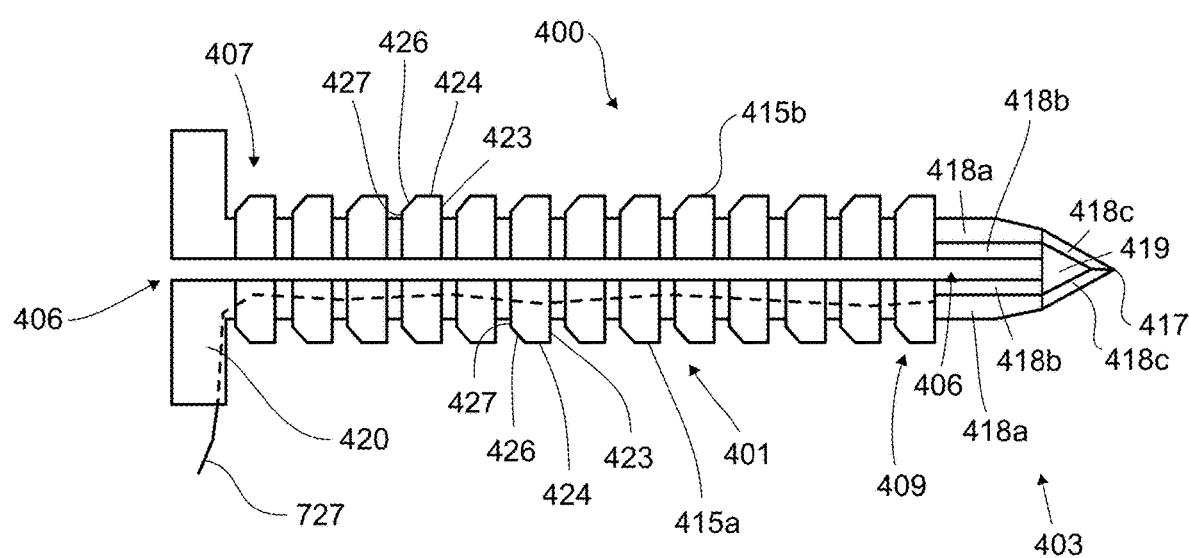
FIG. 4D shows an interior right side view (considering placement of the device on the left side of a person's spine as viewed from their back) of the spinal bone anchor attachment device of FIG. 4A in accordance with one or more aspects and an embodiment of the disclosure.

The tip 403 extends from the second end 409 of the split shaft 401, where the tip also terminates or closes the split 406 in the shaft 401, the tip extending therefrom to a point 417 opposite the base 420. The tip has a plurality of slanted, or faceted, surfaces, or edges, 418a-f and 419 thereon. Thus, on a side of the tip 403 shown in FIG. 4D, adapted to be closer to the spinal cord 120 during installation (an interior side), there are preferably three pairs of faceted surfaces 418a, 418b, 418c, each pair symmetrical relative to the point 417 and the longitudinal centerline of the split shaft 401. The three sets of facet surfaces 418a-c of the interior side of the tip 403 form part of an essentially polygonal shape (such as generally an octagon in cross section—with the split forming opposing two sides of the octagon) for the tip, the tip being adapted for insertion through a properly formed receiving channel 701 (see FIG. 7) which passes through the pedicle bone Ho and into the vertebral body 105.

Further, generally, as the tip 403 reduces in cross-sectional circumferential diameter toward the point 417, it will be appreciated that the various facets 418a-c must also angle inwardly towards the point. Facets 418a and 418b, while on different intersecting planes to approximate the octagonal cross-section shape of the tip, each nevertheless runs parallel to the longitudinal axis of the centerline of the partial shaft 401. Thus, facets 418c are angled along different planes than either of facets 418a and 418b, to narrow the width of the tip down toward the point 417. A central triangular surface 419 is angled downwardly also towards the point 417.

On the opposite, exterior, side of the tip 403 (the side shown in FIG. 4A), the side of the tip further away from the spinal cord 120 during installation, the tip further comprises facets 418d-f Thus, on the exterior side of the tip 403, there are preferably three pairs of faceted surfaces 418d, 418e, 4.18f, each pair symmetrical relative to the point 417 and the longitudinal centerline of the split shaft 401. The three sets of facet surfaces 418d-f of the exterior side of the tip 403 form part of an essentially polygonal shape (such as generally an octagon in cross section—with the split forming opposing two sides of the octagon) for the tip, the tip being adapted for insertion through a properly formed receiving channel 701 (see FIG. 7) which passes through the pedicle bone Ho and into the vertebral body 105.

Further, generally, as the tip 403 reduces in cross-sectional circumferential diameter toward the point 417, it will be appreciated that the various facets 418d-f must also angle inwardly towards the point 417. Facets 418d and 418e, while on different intersecting planes to approximate the octagonal cross-section shape of the tip, each nevertheless runs parallel to the longitudinal axis of the centerline of the partial shaft 401. Thus, facets 418f are angled along different planes than either of facets 418d and 418e, to narrow the width of the tip down toward the point 417. This exterior side of the tip 403 (and in particular facets 418f) are further angled toward the interior side of partial shaft 401 of device 400, and thus this exterior side forms a bias element 405 adapted for guiding proper placement of the anchor attachment device 400 and thereafter the screw 140 into the bone 110, 105. The bias element (418f) may thus have an enhanced angled outer surface for guiding the tip 403 of the anchor device 400 into the bone 110, 105. The tip 403 may be 1 to 3 cm in length as to allow for the tip to be strong enough to guide the device 400 through the bone while at the same time holding the upper and lower portions 411, 413 of the split shaft 401 together at the tip end of the device 400.

Figure 6:
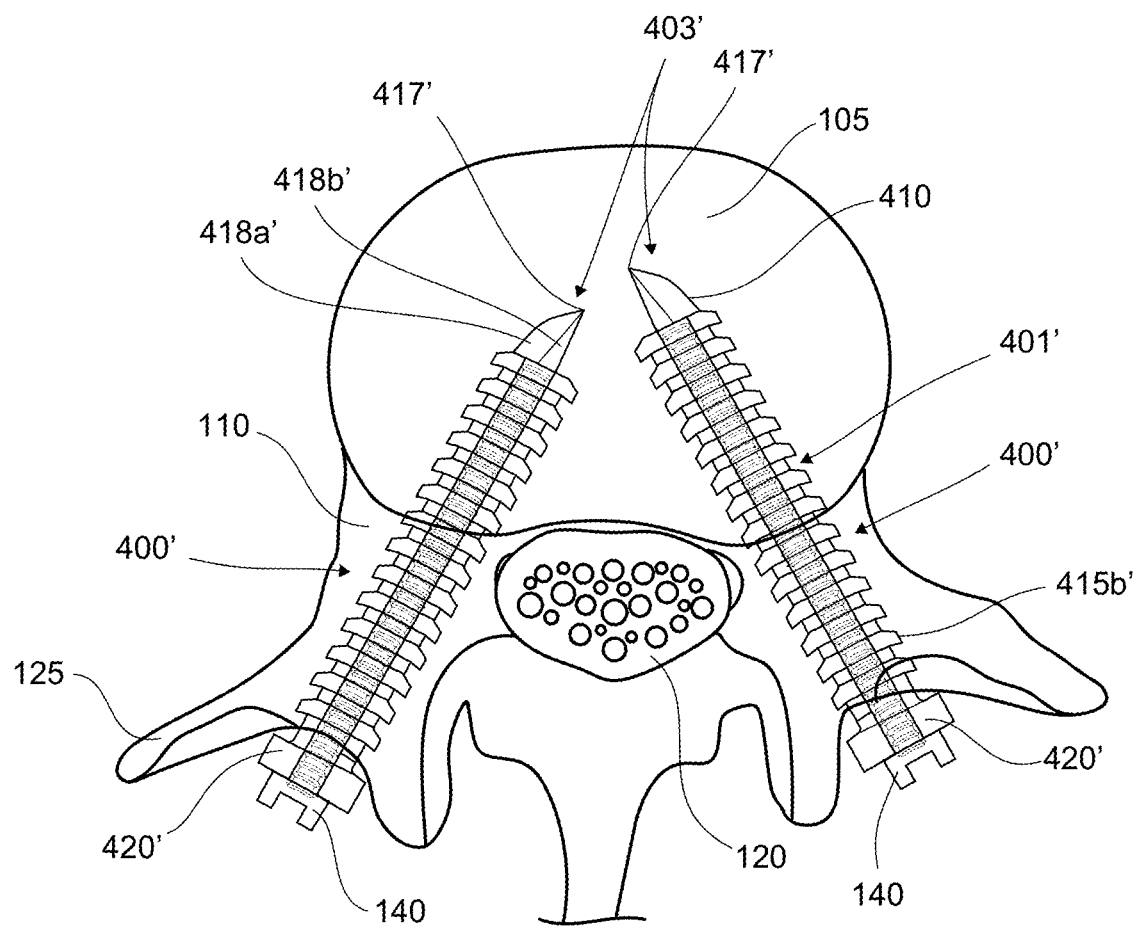
FIG. 6 shows a lateral cross-section top view of a thoracic vertebra and how two alternate spinal bone anchor attachment devices of FIG. 5 in accordance with one or more aspects and an embodiment of the disclosure would be inserted into two properly placed incisions in the vertebra, and with pedicle screws inserted into each device.

Alternatively, as shown in FIG. 6, an exterior side of tip 403' may also comprise a gentle curve 418' made up of two congruent (or mostly congruent) arcs 418a' and 418b' on each side of the tip 403', which run the length of the tip, and end in a point 417'. In such an embodiment, the gentle curve which makes up the tip 403' may be rounded in shape and may resemble a cone made up of two congruent arcs ending in the point 417'. It will be appreciated that a variety of shapes may be used to create the tip 403, 403' which engages the pedicle spinal bone 110, and the vertebral body spinal bone 105, while piercing through them, and the tip is not limited to the shapes shown in FIG. 4A-D, FIG. 6, or described herein.

The plurality courses of bone engaging ridges, or knurling 415a, 415b are adapted to engage and secure attachment between the bone screw 140 and the pedicle bone 110. The bone engaging ridges 415a, 415b in particular may be adapted to engage the cortical surface 113 (see FIG. 3B) of the pedicle bone Ho and the cortical rim 113 of the vertebral body 105 as to facilitate a strong attachment between a pedicle screw 140 inserted into the device 400 and spinal bones 110, 105.

In an embodiment, the bone engaging ridges 415a, 415b each comprise an edge, or surface, 423 extending away from the partial shaft 401 (i.e., preferably, but not necessarily, forming an angle up to go degrees with the partial shaft) and which bends approximately at a 90-degree angle and extends as another edge, or surface, 424 along a line before curving back down to the base 420 as shown in FIGS. 4A and 4B. Thus, each bone engaging ridge 415a, 415b may appear in cross section (i.e., a longitudinally oriented plane relative to the longitudinal length of the device 400) basically as a sawtooth, yet preferably each bone engaging ridge 415a, 415b also extends as a circumferential ridge extending from and around the outer portion 411, 413 of each partial shaft 401.

The go-degree angle of each bone engaging ridge 415a, 415b may thus be placed substantially normal to and against the surface of the pedicle bone 113 as the device 400 is inserted into the receiving channel 701 and a pedicle screw 140 is inserted into the device, causing displacement of the preferably bifurcated split shaft 401, and compression of the bone engaging ridges 415a, 415b against the pedicle's Ho inner cortical bone 113. Described differently, the bone engaging ridges 415a, 415b may appear to slope toward the tip 403 for each course of ridges, and then cut back in at a perpendicular angle relative to the partial shaft 401 of the device 400, so as to be adapted to "bite" into the bone Ho and facilitate maximum interaction and engagement with the bone surface.

Figure 5:
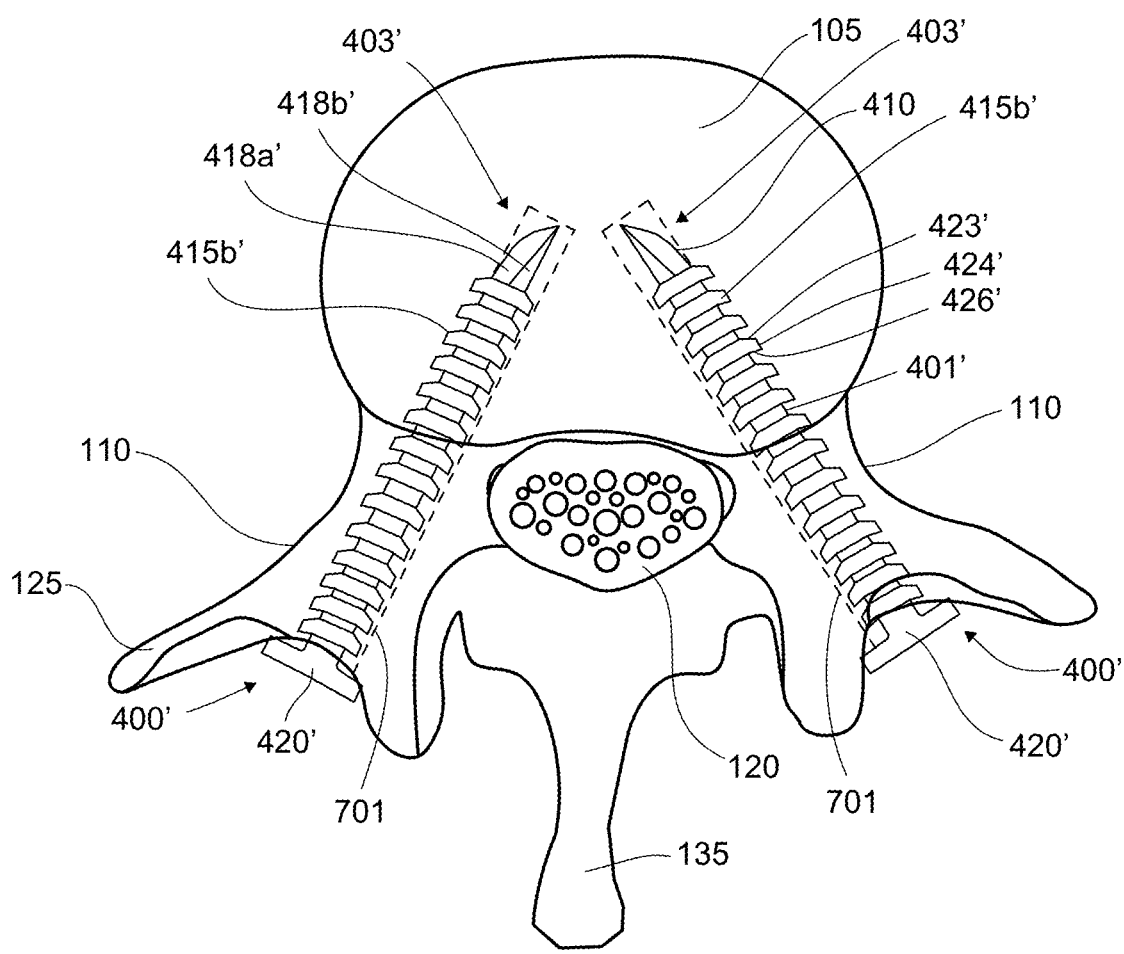
FIG. 5 shows a lateral cross-section top view of a thoracic vertebra and how two alternate embodiment spinal bone anchor attachment devices in accordance with one or more aspects and an embodiment of the disclosure would be inserted into two properly placed incisions in the vertebra.

Alternatively, there are bone engaging ridges 415a', 415b' as shown in FIG. 5, comprising a first edge (or surface) 423' positioned at a rearwardly extending angle (sloping toward the base 420') to the partial split shaft 401' which extends outwardly from the partial split shaft, and a second edge (or surface) 424' which is generally oriented horizontal to the partial split shaft, and a third edge (or surface) 426' extending at an angle back down to connect back to the partial split shaft as shown in FIG. 5. Thus, whereas the bone engaging ridges 415a, 415b have the appearance of angling, or "biting" toward the tip 403, the bone engaging ridges 415a', 415b' have the opposite appearance of angling, or "biting" toward the base 420'. However, it will be appreciated by those skilled in the art that a variety of patterns and shapes may be used to create the bone engaging ridges, or knurling, which are to engage the spinal bone 110, 105, and such alternatives are not limited to the shapes and patterns shown in FIGS. 4A-C, FIG. 5, or otherwise as described herein.

Referring to FIG. 4C, the device 400 (and 400') may further comprise interior screw engaging ridges, or knurling, 427 located at, or adjacent, the inner surface 425 of the device where it will interact with a bone screw 140 inserted into the device. These interior screw engaging ridges 427 preferably comprise a series of ridges 427 which traverse the shaft 401. Where the ridges 427 intersect the split shaft 401, there are intersecting shaft walls 430 (perpendicular to parallel ridges 427), which run the length of the split shaft 401. The ridges 427 and shaft walls 430 may contact a bone screw 140 along the threads of the screw in order to provide an enhanced surface area to facilitate attachment of the screw to the device 400. Thus, there will be provided increased biting capability of the screw 140 along the ridges 427 at those areas where they contact the screw due to a reduced surface area of the ridges relative to an otherwise flat, or smooth curved, surface, and this higher pressure compression will facilitate improved attachment between the screw and the device.

Figure 4E:
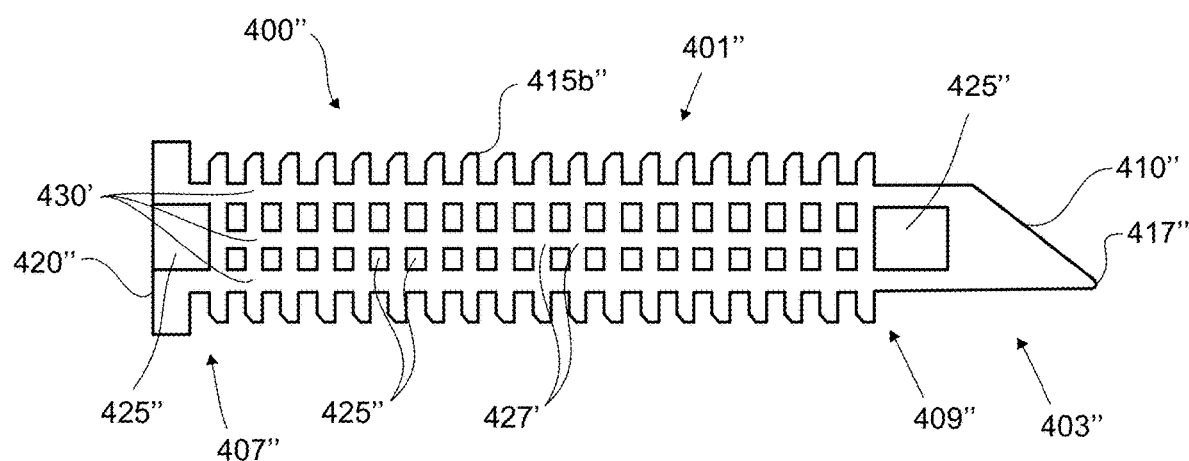
FIG. 4E shows a bottom section view (considering placement of the device on the right side of a person's spine as viewed from their back) of alternative screw engaging knurling, ridges, or lattice-type structure, for an alternative spinal bone attachment device.

As shown in FIG. 4E, there are shown alternative interior screw engaging ridges 427', 430', knurling, or lattice-type structure, having a different pattern, for example wherein the parallel ridge 427' are smaller corresponding to smaller bone engaging ridges 415a'', 415b'', which parallel ridges extend to the inside of the device 400" from the outer bone engaging ridges 415a'', 415b''. Where the parallel ridges 427' intersect the split shaft 401", there are intersecting shaft walls 430' (perpendicular to parallel ridges 427'), which run the length of the split shaft 401". In such an alternative, such a grid of raised ridges 427', 430' will be formed by the intersecting perpendicular ridges, and are adapted to contact the threads of a screw 140 at multiple different angles, from different sides, and will thus provide a compressive force against the screw in multiple different directions. Thus, such perpendicular raised ridges 427' may facilitate increased attachment, or engagement, between the screw 140 and the device 400" by locking the device and screw into place and preventing screw motion following insertion due to the compressive force applied to the screw from multiple different directions, and by allowing the screw threads 115 to penetrate the grid cavities 425' created by the perpendicular raised ridges 427'. The ridges 427' will create an enhanced engagement with the bone screw 140, but they do so in a manner which does not compromise the strength of the body 401" of the device 400". This may be done by adding the ridges 427' on top of the initial thickness of the shaft 401" (the shaft typically being concave at that location), and this may serve to increase the strength of the shaft by providing additional structural support for the body of the shaft. While particular embodiments of the interior knurling are set forth above, a variety of patterns and shapes may be used to create the interior knurling 427, 427' which engages the bone screw 140, and the interior knurling is not limited to the shapes and patterns described herein.

Additionally, the device 400 (or 400', 400") may further comprise a wire tracer 727 (shown in FIG. 4A) which runs the length of the device along the shaft 401, or a wire mesh fabricated coextensive with the surface of, or implanted within, the device as to allow for visualization of the device with medical imaging, and in particular visualization using x-ray imaging.

Referring now more specifically to FIG. 4B, there is shown a bottom view (considering placement of the device on the right side of a person's spine as viewed from their back) of the spinal bone anchor attachment device 400 in accordance with aspects and an embodiment of the device. Thus, shown along a bottom face of the device is one half 411 of the split shaft 401 with the exterior bone engaging ridges 415a preferably continuously running along the bottom of the device 400 from the first end 407 of the split shaft, to the second end 409 of the split shaft. Also shown are what may be considered a bottom-facing portion, or view, of the of the tip 403, thus showing at least faceted surfaces 418b of the interior facing side of the tip 403, and faceted surfaces 418d and 418e visible on the exterior facing side of the tip 403. Thus, in this bottom facing view of the tip 403, the tip may be biased, or slanted, along an exterior-most edge 410 along two opposing upper and lower portions of the device 400, with faceted surfaces 418f symmetrically located about the point 417 and a longitudinal centerline running along the split 406 of the split shaft 401. Accordingly, the exterior-most edge 410 bifurcates the faceted surfaces 418f and forms the exterior-most extent, or edge, comprising the bias element of the tip 403. Alternatively, in such an embodiment where the tip 403' is characterized by a gentle curve 418' made up of two congruent (or mostly congruent) arcs 418a', 418b' on each side of the tip, the bottom facing portion of the tip may show rounded edges around the tip with the congruent arcs intersecting at a point 417' with an interiorly lateral (relative to an extended central longitudinal axis of the split shaft 401) displacement of the point relative to the central longitudinal axis of the split shaft. Thus, the bias of the tip 403' (and 403) and device 400', (and 400), may be clearly seen. This bias helps to ensure that the device not only stays within a properly formed tract 701 in the pedicle 110 and vertebral body 105, but also may be used to help rescue as to an improperly formed tract 703 by helping keep the tip 403' (403) in a subsequently-formed properly formed tract 701.

FIG. 5 shows a lateral cross-sectional view of a thoracic vertebrae with two of the spinal bone anchor attachment devices 400 inserted into two properly placed incisions 701. The spinal bone anchor attachment devices 400 are inserted through the pedicles 110 and into the vertebral body 105, with the slanted edge 410 inserted deep into the inner cancellous bone III (see FIG. 3B) of the vertebral body. The exterior bone engaging ridges 415a, 415b better engage even upper and lower portions of hard weight bearing cortical bone 113 along the pedicle Ho and cortical rim surrounding the vertebral body 105, since as shown and described in connection with FIGS. 9A and 9B, the split shaft 401 of the device 400 is split apart upon installation of the bone screw 140, such that the bone engaging ridges engage the cortical bone. This, in turn, provides for better and more consistent patient outcomes, since the device 400 (400', 400") is less like to loosen over time as it is caused to bite into the cortical bone 113. The device 400 is inserted at an angle away from the spinal cord 120, between the transverse process 125, which protrudes from the pedicle 110, and spinous process 135, which protrudes from the center mass of the spine, through the center of the pedicle Ho as shown by longitudinally running incision line 114 shown in FIG. 3B.

Referring now more specifically to FIG. 6, there is shown a lateral cross-sectional view of a thoracic vertebrae with two alternate embodiment spinal bone anchor attachment devices 400' inserted into two properly placed incisions 701 (not shown), with a pedicle screw 140 inserted into each device. The pedicle screw 140 is inserted into the device 400' at the split 406' in the split shaft 401'. Thus, as with other embodiments, the device 400' is inserted through a pilot hole 701 in the center of the pedicle 110 and into the center mass of the vertebral body 105, and the slanted edge tip 403 is pushed through the bone and guides the placement of the device as previously described such that the threads of the bone screws 115 will engage with the interior knurling 427', (427) of the device 400' (400) to facilitate an improved interaction between the device and the bone screw. And further, as previously described in connection with device 400' (400), the exterior bone engaging ridges 415a, 415b provide additional surface area in a shape designed to maximize the pressure placed upon the cortical bone 113 at the bone engaging ridges (now expanded upon insertion of a pedicle screw 140), which engage with the interior cortial portions 113 of the bone 110, 105, to facilitate improved attachment between the device and the spinal bone.

Figure 7:
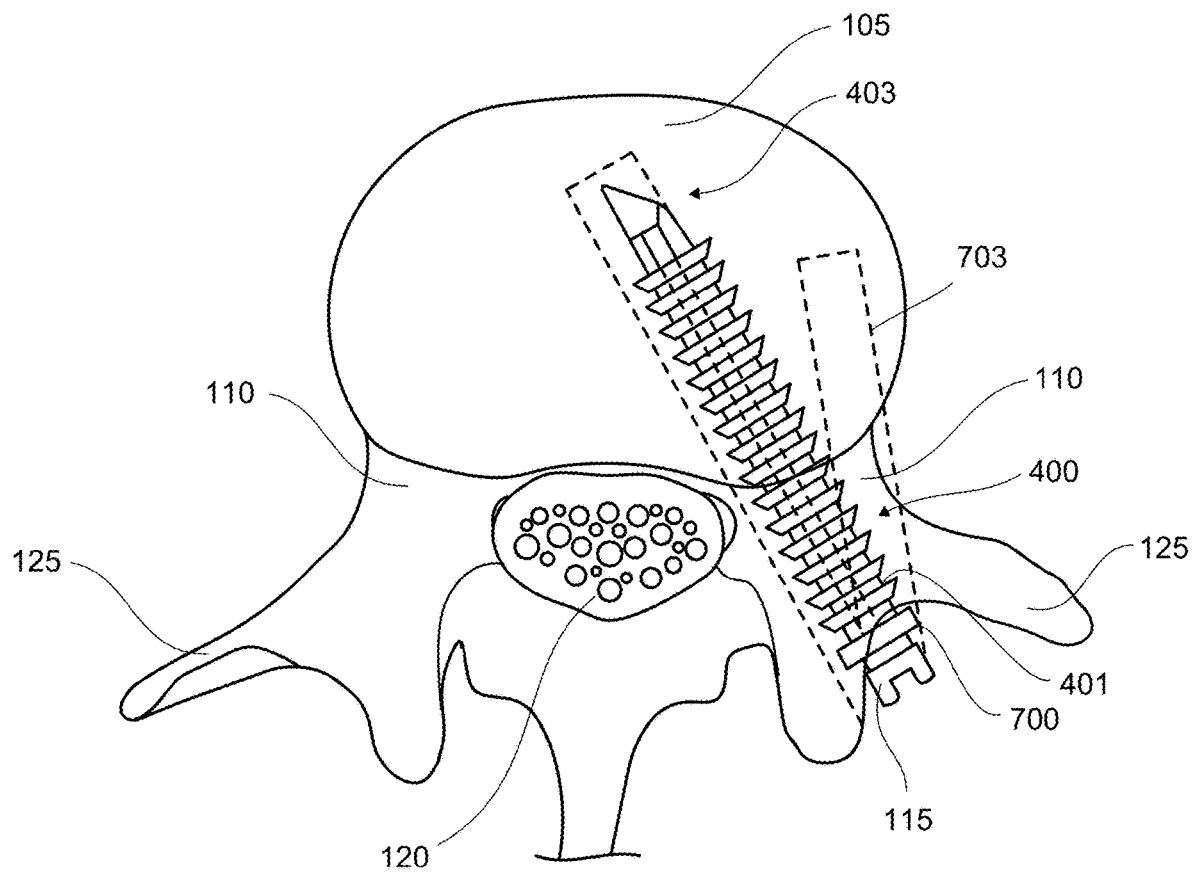
FIG. 7 shows a lateral cross-section top view of a thoracic vertebra and how a spinal bone anchor attachment device would be inserted properly into a properly placed incision and relative to an improperly placed incision in the vertebra.

FIG. 7 shows a lateral cross-section view of a thoracic vertebrae with the spinal bone anchor attachment device 400 inserted properly in a properly placed incision 701, relative to an improperly placed incision 703. Similar to FIG. 6, The pedicle screw 140 is inserted into the device 400 at the split shaft 401, the device 400 is inserted through the incision, essentially a pilot hole, 701 through the center of the pedicle Ho and into the center mass of the vertebral body 105. Properly placed, the incision 701 is created at an angle away from the spinal cord 120 and away from transverse process 125 which protrudes from the pedicle. In this embodiment of the anchor attachment device 400, an exterior portion of the split shaft 401 faces outwardly away from the spinal cord 120 toward the transverse process 125 and covers access to the improperly placed incision 703. This allows for a pedicle screw 140 to be easily inserted into a correct position along incision 701 along the interior screw engaging ridges 427 of the split shaft 401, as there is no tendency for the screw to follow the path of the improperly formed incision 703 due to the improper incision being covered by the anchor device 400. In this way, the anchor device 400 may be said to have rescued installation of the device 400, and subsequent screw 140, from an improper location to a proper one.

Figure 8:
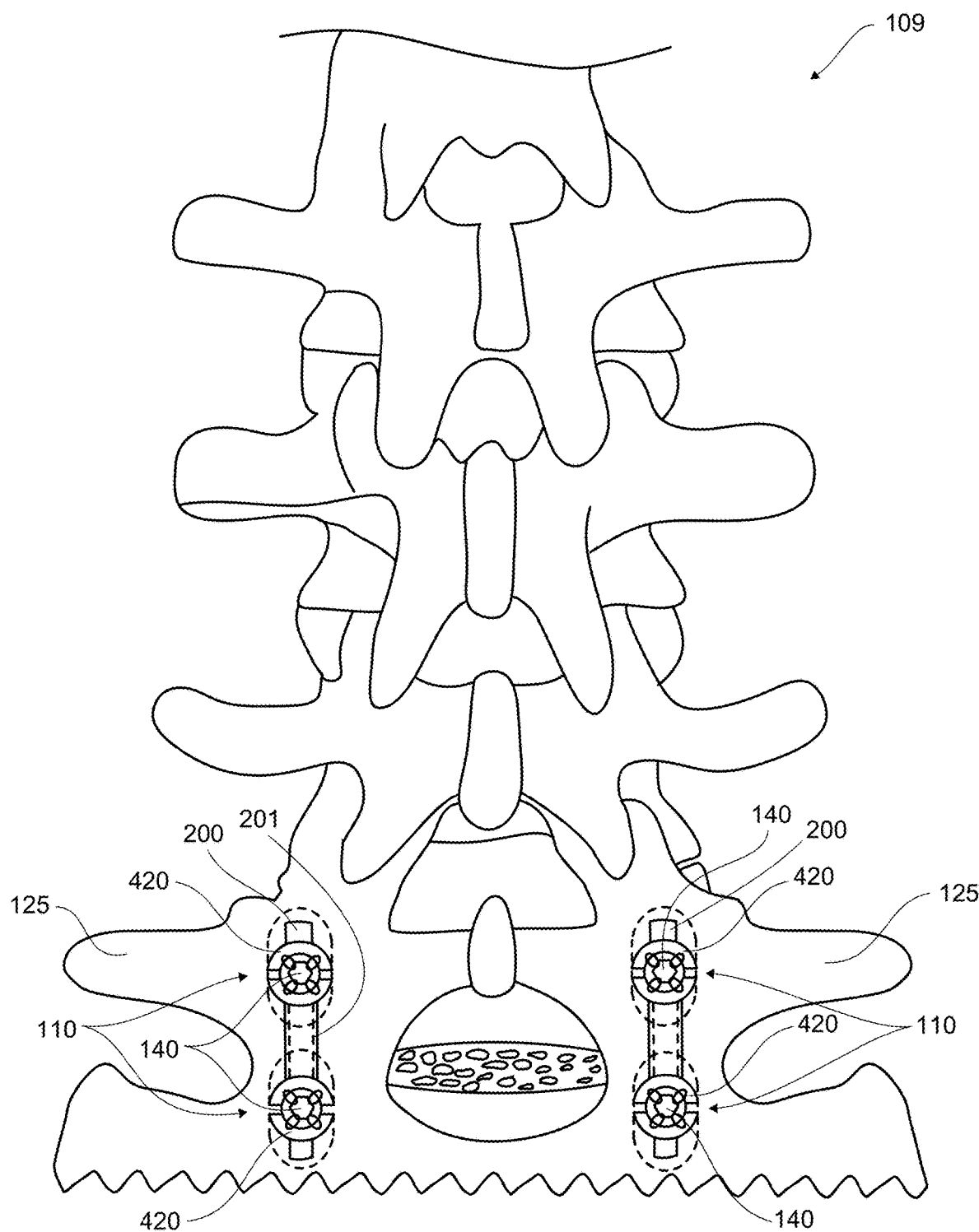
FIG. 8 shows a posterior back view of a portion of a lumbar spine and how four spinal bone anchor attachment devices in accordance with one or more aspects and an embodiment of the disclosure would be inserted having pedicle screws inserted into the devices and the spine as components of an intervertebral stabilization system.

As shown in FIG. 8, the spinal bone anchor attachment device 400 (400', 400") may be used as components, together with pedicle screws 140, inserted into the spine via pedicles 110 as part of an intervertebral stabilization system. The anchor devices 400 facilitate increased attachment between the pedicle screw 140 and the bone by providing an enhanced surface between the screw and the device, and an enhanced engagement of surfaces 415a, 415b of the device 400 and the cortical bone 113. The anchor device 400 (400', 400") is thus adapted to allow for insertion of the pedicle screw 140, while leaving the base 141 of each screw accessible for attachment of cross members 200 and spacers 201 of the intervertebral stabilization system as known in the art.

As a component of such an intervertebral stabilization system, the anchor device 400 (400', 400") may reduce the complications associated with pedicle screws 140 such as vascular and neurological deficits (radicular pain, motor and sensory dysfunction), dural tear, pain, pseudarthrosis, radiculopathy, and pedicle fracture due to instruments loosening and pulling out. Additionally, as a component of such an intervertebral stabilization system, the anchor device 400 (400', 400") may reduce risk of screw failure and pedicle injury due to the screw loosening, screws shifting within the patient, or screws pulling out of the pedicle and/or bending, which may also result in complications to the patient.

In particular the anchor device of present embodiments as part of such an intervertebral stabilization system may deliver a high value to the patient as a component of a long vertebral fusion procedure (e.g. 4-7 vertebrae) where there is a high level of stress placed on the upper pedicle screws due to the load placed upon them by the screws inserted into vertebrae below, and therefore a high risk of screw failure and associated complications. By providing an enhanced surface upon the preferably biocompatible material of an anchor device 400, 400', 400" for a bone screw to attach the device to the screw, and for the device to attach to the bone, as is done by the anchor device of present embodiments, the risk of screw failure is reduced, and patient outcomes are improved.

FIG. 9A shows a longitudinal cross-section side view of the spinal bone anchor attachment device 400, 400', 400" of present embodiments inserted into a pedicle bone 110 without a pedicle screw inserted. FIG. 9B also shows a longitudinal cross-section side view of the spinal bone anchor attachment device 400, 400', 400" of present embodiments with associated displacement as a result of an inserted pedicle screw. The pedicle screw will displace the split shaft 401 of the anchor device 400, and cause the exterior bone engaging ridges 415a, 415b of the device to engage the bone at an enhanced angle relative to the position of the exterior bone engaging ridges without a pedicle screw. Similarly, the interior screw engaging ridges 427 of the device 400 will also engage the pedicle screw threads 115 at an enhanced angle due to the displacement of the split shaft caused by the insertion of the screw 140.

The spinal bone anchor attachment devices 400, 400', 400" of present embodiments may be composed of a variety of compatible biomaterials, such as Ti or PEEK (polyether ether ketone). However, it is desirable to select a biomaterial with an elastic modulus that is similar to that of bone as to resist being damaged by the bone tissue, while also not damaging the surrounding bone tissue. The elastic modulus of a material is a quantity that measures an objects resistance to being deformed when a stress is applied to it. The elastic modulus, also called Young's modulus, is defined as the slope of the stress-strain curve in the elastic deformation region of a material. A material is within the elastic deformation region where it is deformed without being permanently damaged or permanently changing in shape. If a material has an elastic modulus less than that of bone, then the load across the bone tissue will be primarily bore by the bone and not the biomaterial. Conversely if the elastic modulus is greater than that of bone, then the load will primarily be bore by the biomaterial. In particular PEEK is a suitable material for use with bone tissue because it has an elastic modulus of 3.6 GPa.

The average elastic modulus of cancellous bone measured ultrasonically has been reported to be 14.8 GPa, and reported to be 10.4 GPa when measured mechanically. See, J Y Rho, et al., Young's Modulus of Trabecular and Cortical Bone Material: Ultrasonic and Microtensile Measurements, 26(2) J. Biomechanics 111-119 (1993). The average elastic modulus of cortical bone measured ultrasonically has been reported to be 20.7 GPa, and reported to be 18.6 GPa when measured mechanically, and more broadly has been reported to be within the range of 7-30 GPa, as it may vary among patients. See, Id.; Amaral, M., Lopes, et al., Densification route and mechanical properties of $Si_3N_4$-bioglass biocomposites, 23(3) Biomaterials 857-862 (2002). Having an elastic modulus of 3.6 GPa, PEEK is a compatible biomaterial with bone because its elastic modulus is high enough such that it can withstand the pressure placed upon it and surrounding bone tissue following the placement of a pilot hole without permanently damaging the biomaterial, while also not damaging the bone tissue. Since PEEK's elastic modulus of 3.6 GPa is less than that of bone as it has been reported broadly, it does not present a significant risk of damaging the surrounding bone tissue following insertion of the device in almost all patients, thereby making it a suitable biomaterial for use with bone screws.

Ti is also a compatible biomaterial that has been used with some success across various applications in implants, including in bone screws. Despite having an elastic modulus of 113.8 GPa, it has been used with success in bone screws notwithstanding the risk of damaging surrounding bone tissue due to its strong resistance to deformation, evidenced by its high elastic modulus greater than that of bone. Accordingly, it may also be possible to produce the anchor device of present embodiments with Ti.

Other important properties of biomaterials used to fabricate the spinal bone anchor attachment device 400, 400', 400" of present embodiments include hardness, fracture strength, fracture toughness, and fatigue. It is desirable to fabricate the device 400, 400', 400" out of a material with a hardness similar to that of bone, high resistance to fracture, and high resistance to material fatigue. PEEK is a suitable biomaterial for use in bone tissue because it has a hardness similar to that of bone, high resistance to fracture, high fracture toughness, and high resistance to material fatigue.

While particular embodiments of composition of the device are set forth above, a variety of compatible biomaterials may be used to create the device which engages the bone screw, and the composition of the device is not limited to the biomaterials disclosed herein.

The spinal bone anchor attachment devices 400, 400', 400" of present embodiments may be fabricated using a variety of different manufacturing techniques known within the art which are suitable for production of devices using biomaterials, including casting, molding, 3D printing, and other methods.

Also disclosed is a method of using the spinal bone anchor attachment device of present embodiments with bone screws generally and in spinal fusion surgeries. An improved method for the placement of bone screws likely to reduce complications associated with various forms of screw failure which will improve patient outcomes is disclosed. An improved method for placement of bone screws may comprise providing a bone screw, providing a bone anchor attachment device of present embodiments for coupling to a bone screw, making an incision into the bone with a piercing member, which may include a percussion drill designed for drilling bone, the incision extending from the surface of a patient's skin through the cortical bone and into the cancellous region of the bone, preparing the incision for the insertion of the anchor attachment device of present embodiments, inserting the anchor attachment device into the incision at an orientation which will account for the displacement of the split shaft and the associated compressive force placed on the bone in at least two opposing directions, inserting the bone screw into the anchor device, and tightening the screw and anchor device into place as necessary.

When selecting the orientation of the anchor bone anchor attachment device 400, 400', 400" of present embodiments, the orientation will depend on the location of where the screw is being inserted into the body. For instance, if it is a pedicle screw being inserted into the spine, it is important that the device be inserted with the split shaft portions III, 113 being upwardly oriented (toward the patient's head) and downwardly oriented (toward the patient's feet) into and along a longitudinal axis 114 (see FIG. 3B) of the pedicles iio of the patient's spine as to cause displacement of the split shaft upwards and downwards into the pedicle, parallel to the direction of the spine along the weight bearing axis of the spine, and not side to side perpendicular to the weight bearing axis of the bone which may push the bone apart towards the spine and potentially injure the patient.

When selecting the proper orientation of the bone anchor device 400, 400', 400", the weight bearing axis of the bone at issue should be considered, as well as the anatomy of the area. For instance a bone screw placed into the tibia below the knee should be inserted with the split shaft perpendicular to the length of the bone, such that the displacement of the split shaft will occur vertically, parallel to, and along the length of the bone in the direction in which it bears weight. Similarly, if the device were being used for a hip screw inserted into the femur, the device should be inserted with the split shaft perpendicular to the length of the bone, such that the displacement of the split shaft would occur vertically, parallel to, and along the length of the bone in the direction in which it bears weight.

In accordance with the foregoing description and Figures, it will be appreciated that lateral positioning of a device 400, 400', 400" as described herein helps strengthen the engagement of a pedicle screw 140 to the cortical bone 113 of the pedicle area 110 (and entering into the vertebral body 105) as it passes along the axis 114 of the pedicle, and the device may also be helpful in rescuing an incorrectly formed tract 703 through the pedicle.

In the preceding description, numerous details were set forth. It will be apparent, however, to one skilled in the art, that the present invention may be practiced without some of these specific details. Additionally, one of ordinary skill in the art will recognize the inventive principles disclosed are not limited to the embodiments disclosed herein, and that various aspects of the disclosed embodiments can be combined to achieve yet additional embodiments. In some instances, well-known structures and devices are shown in block diagram form, rather than in detail, in order to avoid obscuring the present invention.

The anchor device and methods of the present disclosure address problems with prior art devices and methods of risks of failure and negative patient outcomes. This is because the present device and methods help to alleviate inadequate surface area interaction between the hard-cortical bone of prior art devices and methods. Thus, the present device and methods will enhance positive patient outcomes in many cases, and especially in challenging cases of long vertebral fusions using pedicle screws.

Thus, while a preferred embodiment of the present disclosure has been shown and described, it will be apparent to those skilled in the art that many changes and modifications may be made without departing from the claimed subject matter in its broader aspects. For example, it will be appreciated that one of ordinary skill in the art may mix and match the various components of the various embodiments of the claimed subject matter without departing from the true spirit of the claims. The appended claims are therefore intended to cover all such changes and modifications as fall within the true spirit and scope of the invention.

What is claimed is:

1. A spinal bone anchor attachment device adapted for use with a pedicle screw, comprising:
an elongated multi-laterally split partial base portion split along, and adapted for insertion of the pedicle screw along, a central longitudinal axis of said partial base portion;
an elongated multi-laterally split partial shaft portion split along, and adapted for insertion of the pedicle screw along, a central longitudinal axis of said partial shaft portion, said partial shaft portion being split into at least a first side and a second side;
an elongated concave inner surface within said partial shaft portion adapted for engaging the pedicle screw;
a biased tip portion having a displaced tip and connecting the first side and the second side of the split partial shaft portion, said biased tip portion comprising a leading first end of the spinal bone anchor attachment device, said biased tip portion being positioned opposite said partial base portion, wherein the displaced tip of said biased tip portion is displaced relative to the central longitudinal axis of the split partial shaft portion and thereby adapted for biased guiding of the spinal bone anchor attachment device and the pedicle screw into the spinal bone; and
a plurality of courses of bone engaging ridges extending outwardly from and along at least a portion of the length of said partial shaft portion, wherein said partial base portion, said partial shaft portion, and said tip, are adapted to cause the anchor attachment device to expand apart upon subsequent installation of the pedicle screw to better engage an inner cortical bone portion of the pedicle, and thereby enhance sturdiness of the vertebral stabilization procedure.

2. The spinal bone anchor attachment device of claim 1, wherein at least one of said plurality of courses of bone engaging ridges is comprised of a plurality of edges, wherein at least one edge of said plurality of edges is positioned normal to said partial shaft portion and extends outwardly from said partial shaft portion.

3. The spinal bone anchor attachment device of claim 1, wherein at least one of said plurality of courses of bone engaging ridges is comprised of a plurality of surfaces, wherein at least one surface of said plurality of surfaces is positioned normal to said partial shaft portion and extends outwardly from said partial shaft portion.

4. The spinal bone anchor attachment device of claim 2, wherein said split partial shaft portion further comprises interior screw engaging ridges which intersect with said split partial shaft portion.

5. The spinal bone anchor attachment device of claim 1, wherein the anchor is composed of PEEK.

6. The spinal bone anchor attachment device of claim 1, wherein each of said plurality of courses of bone engaging ridges extends along only each the first side and the second side of said partial shaft portion.

7. The spinal bone anchor attachment device of claim 1, wherein each of said plurality of courses of bone engaging ridges is equidistant from another of said plurality of bone engaging ridges.

8. The spinal bone anchor attachment device of claim 7, wherein said plurality of courses of bone engaging ridges comprises between 12 and 18 courses of bone engaging ridges.

9. A spinal bone anchor attachment device adapted for use with a pedicle screw, comprising:
an elongated multi-laterally split partial base portion split along, and adapted for insertion of the pedicle screw along, a central longitudinal axis of said partial base portion;
an elongated multi-laterally split partial shaft portion split along, and adapted for insertion of the pedicle screw along, a central longitudinal axis of said partial shaft portion, said partial shaft portion being split into at least a first side and a second side;
an elongated concave inner surface within said partial shaft portion adapted for engaging the pedicle screw;
a tip connecting the first side and the second side, said tip being positioned opposite said partial base portion; and
a plurality of courses of bone engaging ridges extending outwardly from and along at least a portion of the length of said partial shaft portion, wherein said partial base portion, said partial shaft portion, and said tip, are adapted to cause the anchor attachment device to expand apart upon subsequent installation of the pedicle screw to better engage an inner cortical bone portion of the pedicle, and thereby enhance sturdiness of the vertebral stabilization procedure, wherein said tip further comprises a point at a leading end of said tip, a first plurality of faceted interior surfaces, each of said first plurality of faceted surfaces extending partially from corresponding ones of each the first side and the second side of said partial shaft and partially from said tip towards said point, and a second plurality of differently faceted interior surfaces which are interconnected with but non-coplanar with said first plurality of faceted surfaces, each of said second plurality of faceted surfaces extending from corresponding ones of said first plurality of faceted surfaces to said partial shaft portion.

10. The spinal bone anchor attachment device of claim 9, wherein said first plurality of faceted surfaces is symmetrical relative to said point and the first side and the second side of said partial shaft portion, and wherein said second plurality of faceted surfaces are symmetrical relative to the point and the first side and the second side of said partial shaft portion.

11. The spinal bone anchor attachment device of claim 9, wherein said tip further comprises a third plurality of exterior faceted surfaces extending from one of each the first side and the second side of said partial shaft towards said point.

12. The spinal bone anchor attachment device of claim 11, wherein said tip further comprises a fourth plurality of exterior faceted surfaces differently slanted than said third plurality of exterior faceted surfaces and extending from corresponding ones of said third plurality of exterior faceted surfaces to said point, wherein portions of said first and second pluralities of interior faceted surfaces form medial edges with portions of the third and fourth pluralities of exterior faceted surfaces, and wherein said plurality of bone engaging ridges extend outwardly from and along the entire length of said partial shaft portion.

13. A spinal bone anchor attachment device adapted for use with a pedicle screw, comprising:
an elongated multi-laterally split partial base portion split along, and adapted for insertion of the pedicle screw along, a central longitudinal axis of said partial base portion;
an elongated multi-laterally split partial shaft portion split along, and adapted for insertion of the pedicle screw along, a central longitudinal axis of said partial shaft portion, said partial shaft portion being split into at least a first side and a second side;

an elongated concave inner surface within said partial shaft portion adapted for engaging the pedicle screw;

a tip connecting the first side and the second side, said tip being positioned opposite said partial base portion, and wherein said tip further comprises a bias element adapted for guiding proper placement of the anchor attachment device and the screw into the spinal bone; and a plurality of courses of bone engaging ridges extending outwardly from and along at least a portion of the length of said partial shaft portion, wherein said partial base portion, said partial shaft portion, and said tip, are adapted to cause the anchor attachment device to expand apart upon subsequent installation of the pedicle screw to better engage an inner cortical bone portion of the pedicle, and thereby enhance sturdiness of the vertebral stabilization procedure, wherein the bias element comprises an enhanced angled outer surface of said tip relative to said partial shaft portion and adapted for enhanced guiding of the spinal bone anchor attachment device and the screw to proper placement during installation into the pedicle.

* * * * *